(12) United States Patent
Ahrens et al.

(10) Patent No.: US 11,553,940 B2
(45) Date of Patent: Jan. 17, 2023

(54) ARTICULATING SURGICAL INSTRUMENTS SUCH AS RONGEURS

(71) Applicant: Spinal Stabilization Technologies, Dublin (IE)

(72) Inventors: Michael Ahrens, Neustadt (DE); Ralph Duerr, Neuhausen ob Eck (DE)

(73) Assignee: SPINAL STABILIZATION TECHNOLOGIES, Dublin (IE)

( * ) Notice: Subject to any disclaimer, the term of this patent is extended or adjusted under 35 U.S.C. 154(b) by 687 days.

(21) Appl. No.: 16/477,780

(22) PCT Filed: Jan. 12, 2018

(86) PCT No.: PCT/EP2018/050783
§ 371 (c)(1),
(2) Date: Jul. 12, 2019

(87) PCT Pub. No.: WO2018/130663
PCT Pub. Date: Jul. 19, 2018

(65) Prior Publication Data
US 2019/0336157 A1 Nov. 7, 2019

Related U.S. Application Data

(60) Provisional application No. 62/453,129, filed on Feb. 1, 2017.

(30) Foreign Application Priority Data

Jan. 13, 2017 (EP) .................................... 17151467

(51) Int. Cl.
*A61B 17/29* (2006.01)
*A61B 17/295* (2006.01)
(Continued)

(52) U.S. Cl.
CPC ........ *A61B 17/295* (2013.01); *A61B 17/1606* (2013.01); *A61B 17/29* (2013.01);
(Continued)

(58) Field of Classification Search
CPC ................ A61B 2017/2919; A61B 2017/2927
See application file for complete search history.

(56) References Cited

U.S. PATENT DOCUMENTS

| 4,880,015 | A | * | 11/1989 | Nierman | ................ | A61B 10/06 600/564 |
| 5,282,826 | A | * | 2/1994 | Quadri | ........... | A61B 17/320016 81/387 |
| 5,330,502 | A | * | 7/1994 | Hassler | ................. | A61B 17/29 606/174 |
| 5,383,888 | A | * | 1/1995 | Zvenyatsky | ........... | A61B 17/29 606/174 |

(Continued)

OTHER PUBLICATIONS

International Search Report; priority document.

*Primary Examiner* — Nicholas W Woodall
(74) *Attorney, Agent, or Firm* — Greer, Burns & Crain, Ltd.

(57) ABSTRACT

An articulating surgical implement (1) comprising: an elongate body (2) having a proximal end (4) and a distal end (5) and a longitudinal axis (6); a grip (7) on the proximal end for holding the surgical implement; a surgical implement head (8) formed on the distal end of the elongate body, and having surgical implement jaws (10, 11), the surgical implement head having a first joint (13) It that allows the surgical implement jaws to move relative to each other to open and close for gripping or cutting; a second joint (12) on the distal end of the elongate body for changing the angle of the surgical implement head relative to the longitudinal axis of the elongate body; a mechanism comprising a control lever (35), a control rod (39) and a linkage arm (40) for changing the angle of the surgical implement head relative to the longitudinal axis of the elongate body through an angular range of movement by pivoting about an axis of rotation of the second joint; and a mechanism comprising a pulley (Continued)

wheel (50) and a push/pull wire (51) for opening and closing the surgical implement jaws. The surgical implement head may be a rongeur and is operable at 90 degrees to the elongate body in either an upbite or downbite position. It has an angular range of movement of 180 degrees. A desired angle of the surgical implement head is selected by a user, for example for tissue removal from a target site.

14 Claims, 8 Drawing Sheets

(51) Int. Cl.
*A61B 17/16* (2006.01)
*A61B 17/32* (2006.01)

(52) U.S. Cl.
CPC ........... *A61B 2017/2903* (2013.01); *A61B 2017/2927* (2013.01); *A61B 2017/320008* (2013.01)

(56) References Cited

U.S. PATENT DOCUMENTS

| | | | |
|---|---|---|---|
| 5,827,323 A * | 10/1998 | Klieman | A61B 17/2909 606/205 |
| 6,592,572 B1 * | 7/2003 | Suzuta | A61B 17/062 606/1 |
| 2004/0199147 A1 * | 10/2004 | Nishizawa | A61B 17/062 606/1 |
| 2007/0208375 A1 * | 9/2007 | Nishizawa | A61B 17/2909 606/205 |
| 2009/0198272 A1 | 8/2009 | Kerver et al. | |
| 2010/0030029 A1 | 2/2010 | Markham | |
| 2011/0087269 A1 | 4/2011 | Stokes et al. | |
| 2012/0209315 A1 * | 8/2012 | Amat Girbau | A61B 34/71 606/207 |
| 2015/0032151 A1 * | 1/2015 | Ishida | A61B 17/29 606/205 |
| 2016/0100882 A1 | 4/2016 | Boudreaux et al. | |
| 2016/0199087 A1 | 7/2016 | Borden et al. | |

* cited by examiner

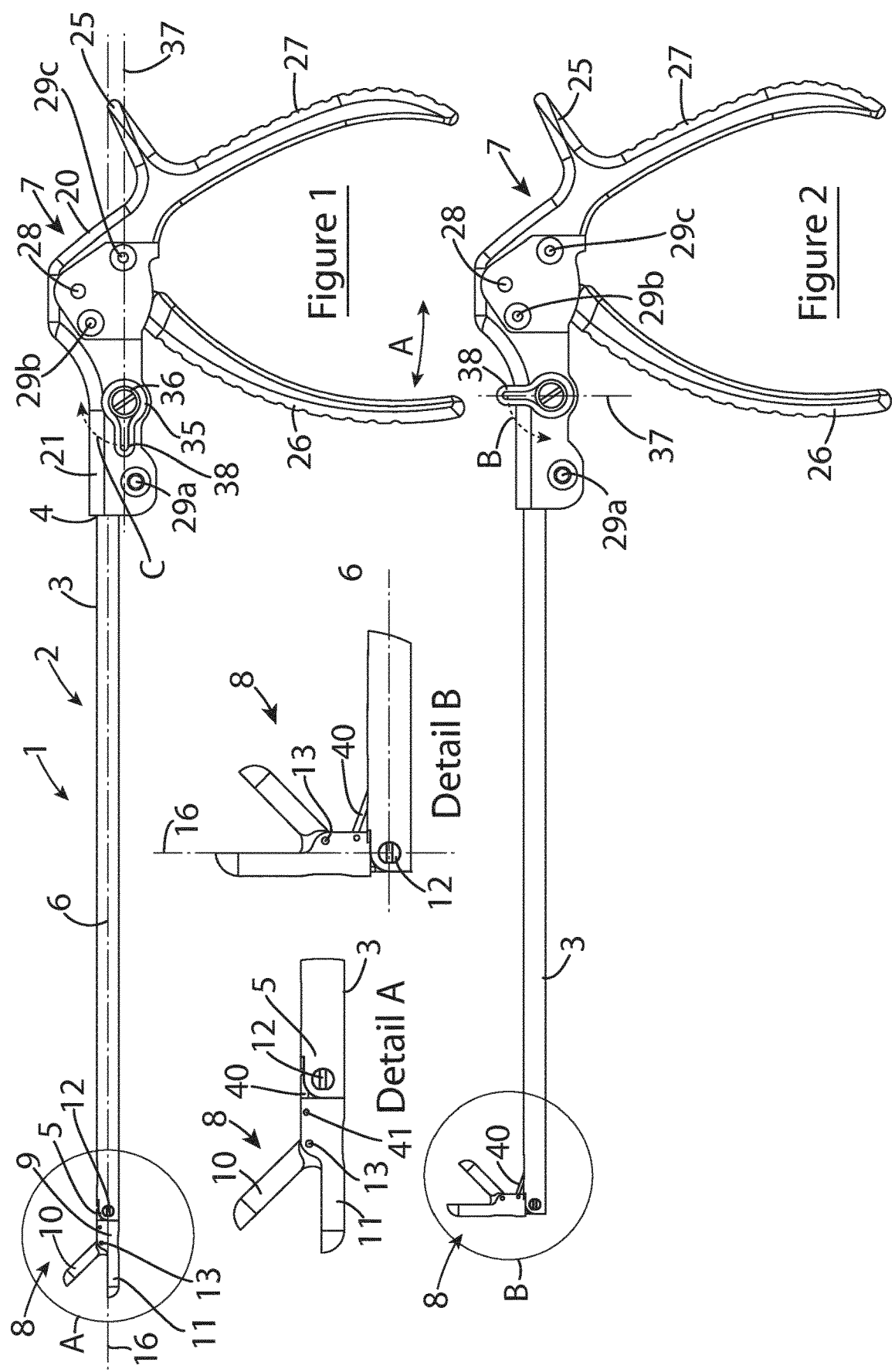

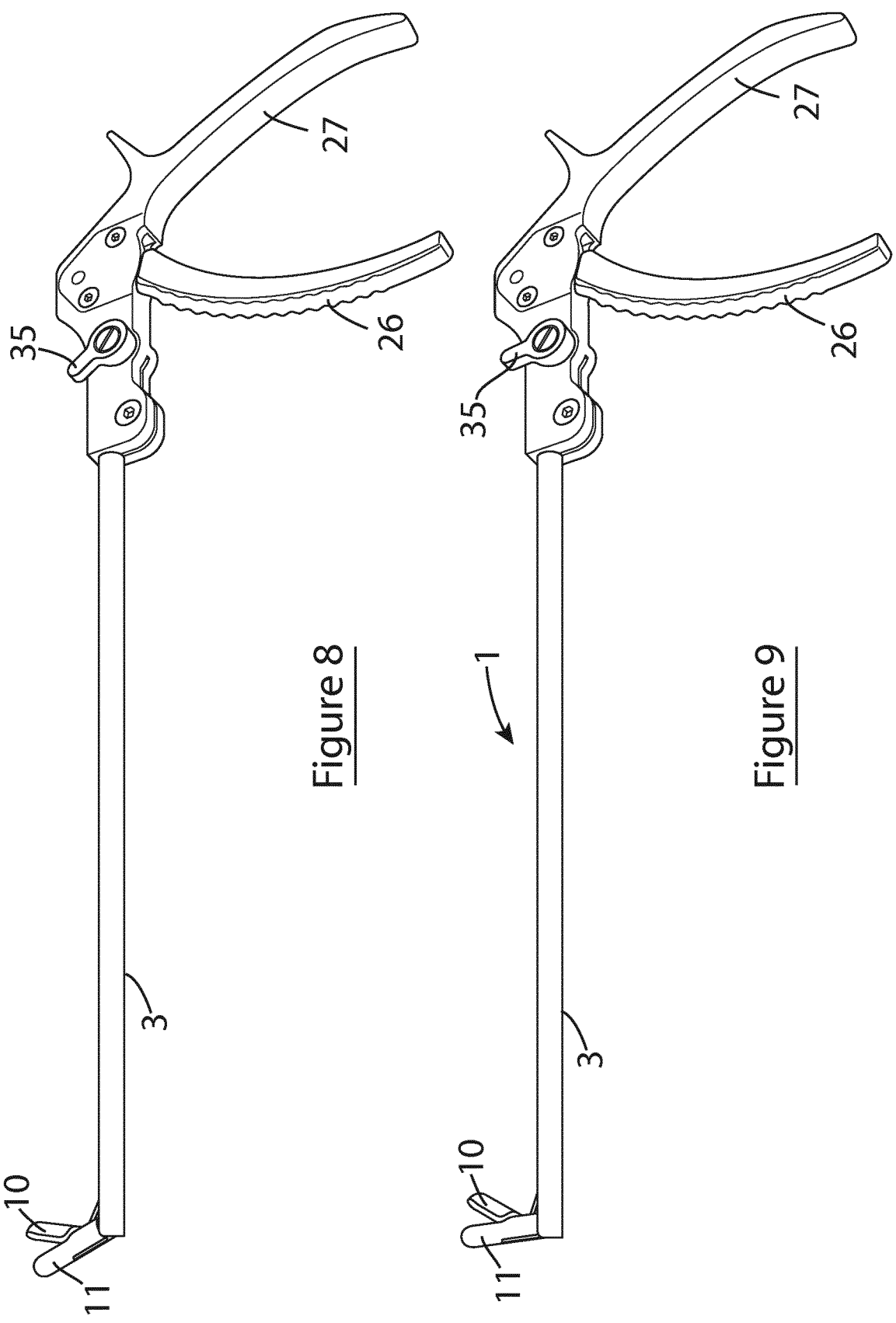

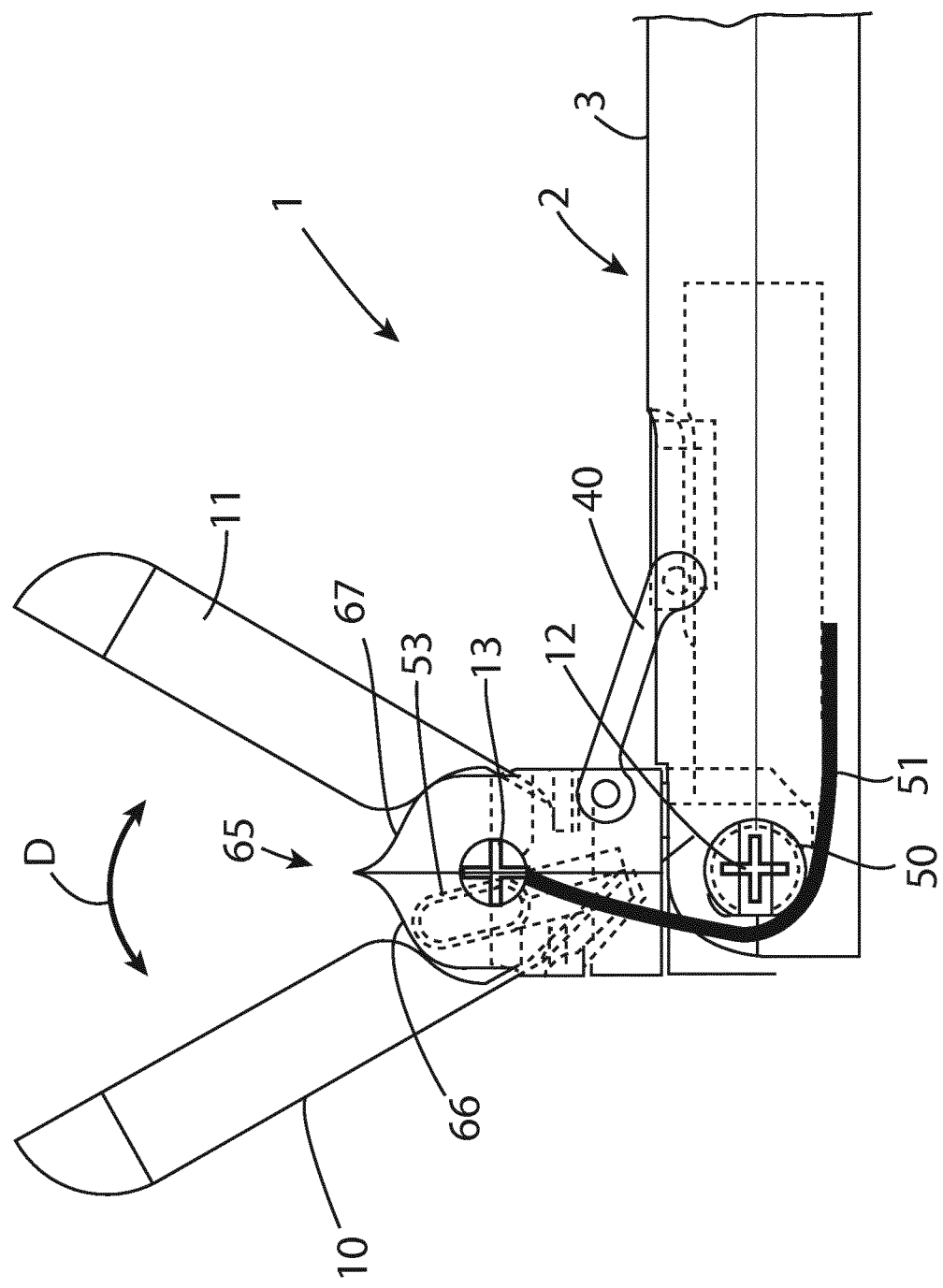

ARTICULATING SURGICAL INSTRUMENTS SUCH AS RONGEURS

CROSS REFERENCES TO RELATED APPLICATIONS

This application is a United States National Stage Application under 35 U.S.C. Section 371 of International Patent Application No. PCT/EP2018/050783 filed on Jan. 12, 2018, claiming priority to European Patent Application No. 17151467.2 filed on Jan. 13, 2017 and U.S. Provisional Patent Application No. 62/453,129 filed on Feb. 1, 2017, all of which are hereby incorporated by reference as if fully set forth herein.

FIELD OF THE INVENTION

The present invention relates to a surgical instrument such a rongeur.

BACKGROUND TO THE INVENTION

It is known to provide surgical instruments for gripping or cutting tissue such as a clamp or a rongeur. A rongeur is utilised to cut away bodily material such as tissue including bone tissue. In such surgical instruments a construction similar to a pliers or scissors is employed; two crossing handles are hinged together and can be moved together to close, and moved apart to open, clamping jaws or sharp cutting jaws. The jaws are used to clamp tissue or cut into and remove material such as tissue. A rongeur is often used to cut into and remove bone.

It is known to provide a rongeur with a single hinge where the opening and closing of the jaws is effected by opening and closing of crossed handles about a single hinge. This is achieved by the opening or closing of crossed handles pivoted like the two halves of a pair of scissors in the manner of a scissors action.

For mechanical advantage, and in particular to reduce the force required to work the instrument, it is known to provide a rongeur with a double hinge arrangement where a first set of jaws hinged about a first pivot open and close a second set of jaws hinged about a second pivot, in the manner of a double scissors action. In such an arrangement each jaw of the first set of jaws is pivotally connected to one jaw of the second set of jaws. Operation of the handles opens and closes the first jaws which in turn opens and closes the second jaws. The second set of jaws are those used for cutting. The first set of jaws is utilised only to effect movement of the second set of jaws.

It is also known to provide rongeurs with an offset bite. An offset bite is where the cutting action takes place at a position angled relative to the remainder of the device for example where jaws are angled relative to the remainder of the device. For example an upbite rongeur is one where the cutting action takes place at a position angled upwardly relative to the remainder of the device, for example jaws that are angled upwardly relative to the remainder of the device, and in particular relative to the position at which the rongeur is held, for example relative to handles that are opened or closed to effect opening or closing of the jaws. A downbite rongeur is one where the cutting action takes place at a position angled downwardly relative to the remainder of the device for example one where jaws are angled downwardly relative to the remainder of the device and in particular relative to the position at which the rongeur is held for example relative to handles that are opened or closed to effect opening or closing of the jaws.

In simple terms an offset bite is one that allows a user to work around a corner. An upbite may be considered to be the arrangement where the instrument removes material at a position above its longitudinal axis and a downbite is where the instrument removes material at a position below its longitudinal axis. Of course it is also the case that rongeurs have been provided that have a straight or non-offset bite - the instrument removes material at a position substantially aligned with its longitudinal axis.

For various applications rongeurs with different offsets may be utilised. For example one may start with a non-offset (or straight) rongeur to remove material that is aligned with the direction of access, and then use progressively more offset rongeurs to access material that is offset (around a corner) from the direction or point of access. In this way tissue that is not accessible with a non-offset rongeurs can be better accessed for removal.

Indeed certain surgical procedures set out in detail how specific areas of tissue can be removed by a set of specific rongeurs. For example one procedure for removal of spinal disc material specifies the use of seven different rongeurs with straight bite and differing offset bites to access and remove all target material based on accessing the target site from the same place each time.

US Patent Publication No. 2002/0138091 describes an apparatus and method for removing intervertebral disc material, such as nucleus pulposus, from a patient. The tissue removal mechanism includes a cannula adapted to be inserted into an intervertebral disc and has an open distal tip. The mechanism further includes a rotatable element having a distal portion with projections or threading, for example, having a substantially helical configuration designed to urge nucleus material into the cannula upon rotation of the rotatable element. The cannula and the rotatable element can be manually deformed so a user can choose to operate it in a straight or curved configuration.

US Patent Publication No. 2002/0165550 describes devices and instruments for implant insertion through a posterior lateral opening to the disc space. It discloses a reamer that can transmit rotary cutting torque through a bend. It describes a shaver with rotating shaving blades that can be advanced about a bend towards a stop. A guided chisel is also described.

US Patent Publication No. 2006/135959 describes nuclectomy method for creating a nuclear cavity in an annulus located in an intervertebral disc space and for preparing the nuclear cavity to receive an intervertebral prosthesis.

SUMMARY OF THE INVENTION

In one aspect, the present invention provides an articulating surgical implement comprising:
(i) an elongate body having a proximal end and a distal end and a longitudinal axis;
(ii) a grip on the proximal end for holding the surgical implement;
(iii) a surgical implement head formed on the distal end of the elongate body, and having surgical implement jaws, the surgical implement head having a first joint that allows the surgical implement jaws to move relative to each other to open and close for gripping or cutting;
(iv) a second joint on the distal end of the elongate body for changing the angle of the surgical implement head relative to the longitudinal axis of the elongate body;

(v) a mechanism for changing the angle of the surgical implement head relative to the longitudinal axis of the elongate body through an angular range of movement by pivoting about an axis of rotation of the second joint; and (vi) a mechanism for opening and closing the surgical implement jaws.

This is a simple construction which is highly manoeuvrable/adaptable. The user can pre-set or preselect any desired position in the angular range of movement at which to operate the surgical implement of the invention.

A device of the invention can be constructed with very small dimensions and thus access sites with very restricted access or cross sectional area.

For example it is possible to construct a device of the invention so that the surgical implement head (when the jaws are closed) has a maximum diameter of about 6 mm for example a maximum diameter of about 4 mm. Desirably the elongate body has a maximum diameter of about 6 mm for example a maximum diameter of about 4 mm.

The mechanism for opening and closing the surgical implement jaws is operable through the angular range of movement.

The present invention provides a surgical instrument such as a rongeur with the capability to articulate a first joint from 90° to −90° and with a second joint distant from the first for manipulating the jaw for opening and closing/ biting. In such an arrangement the present invention allows a total range of movement of 180 degrees to be swept out by articulation of the surgical implement head. The surgical implement head can thus move through a total arc of 180 degrees. For example when sweeping out a semicircular arc a line joining the two ends of the arc is desirably at right angles to the longitudinal axis of the elongate body.

The present invention has provided a mechanism that allows a user to operate the jaws around a 90 degree angle when two spaced apart joints are involved.

One of primary applications of the present invention is to provide an instrument, in particular a rongeur that can be used for removing disc material such as when performing a TNR (Total Nucleus Removal) for example in a nucleus replacement procedure.

The surgical instrument of the present invention is very useful for posterolateral surgical access.

In the present invention the transfer of force to open and close the jaws is transferred over two separate joints.

The present invention supersedes the requirement for a set of surgical instruments with differing offsets, such as has been described above. In particular because a user can select an angular offset (or none) the surgical instrument is adjustable by a user so that the surgical instrument head is at a desired angle.

The technology of the present invention is useful in any surgical application with confined working space where a highly mobile and articulating instrument would be of benefit. Such surgical applications include in ENT (ears nose & throat), neurosurgery, heart surgery and others.

The jaws of the surgical instrument can be configured, for gripping or clamping, for example in forceps, for cutting such as with scissors jaws or cupped cutting jaws. A rongeur generally has cupped cutting jaws for removing portions or bites of tissue.

In the present invention the term jaws includes clamping jaws, cutting jaws and punch action jaws. Likewise the term cutting includes punching.

In the present invention only one jaw may move. Both may move. Where both move they may move by different amounts.

As above the present invention provides an articulating surgical implement according to the invention wherein the angular range of movement is 90 degrees relative to the longitudinal axis of the elongate body so that the surgical implement head can be moved to a position where its longitudinal axis is at 90 degrees to the longitudinal axis of the elongate body.

The surgical implement head is desirably moveable between a straight position where its longitudinal axis is substantially parallel to the longitudinal axis of the elongate body and an angled position where its longitudinal axis is at 90 degrees to the longitudinal axis of the elongate body.

Desirably the angular range of movement is 180 degrees relative to the longitudinal axis of the elongate body so that the surgical implement head can be moved from a first position where its longitudinal axis is at 90 degrees to the longitudinal axis of the elongate body to a second position which is 180 degrees apart from the first position, where its longitudinal axis is (again) at 90 degrees to the longitudinal axis of the elongate body.

The mechanism for changing the angle of the surgical implement head relative to the longitudinal axis of the elongate body may include a first rod, and pushing or pulling the first rod, changes the angle of the surgical implement head relative to the longitudinal axis of the elongate body, by causing it to pivot about an axis of rotation of the second joint. This is a simple construction which allows for manual operation by a user.

This mechanism can be duplicated so that there is a first mechanism for moving the surgical implement head to an upbite position and a second for moving it to a downbite position. For example the mechanism for changing the angle of the surgical implement head relative to the longitudinal axis of the elongate body may include a second rod, and pushing or pulling the second rod, changes the angle of the surgical implement head relative to the longitudinal axis of the elongate body, by causing it to pivot about an axis of rotation of the second joint in a direction opposite to the first rod. However it will be appreciated that a single rod may be used to effect movement towards an upbite or a downbite position.

The mechanism for changing the angle of the surgical implement head relative to the longitudinal axis of the elongate body desirably includes a linkage arm that is pivotably connected to the surgical implement head. Desirably the mechanism for changing the angle of the surgical implement head relative to the longitudinal axis of the elongate body includes a second linkage arm that is pivotably connected to the surgical implement head causing it to pivot about an axis of rotation of the second joint in a direction opposite to the first linkage arm.

The mechanism for changing the angle of the surgical implement head relative to the longitudinal axis of the elongate body suitably includes:

(i) a push-pull rod; and (ii) a linkage arm that is pivotably connected both to the surgical implement head and to the push-pull rod, wherein pushing or pulling the push-pull rod, pushes or pulls the linkage arm, and the linkage arm in turn changes the angle of the surgical implement head relative to the longitudinal axis of the elongate body, by causing it to pivot about an axis of rotation of the second joint. Again this mechanism can be duplicated so that there is a first mechanism for moving the surgical implement head to an upbite position and a second for moving it to a downbite position.

For example in the invention there may be a mechanism for changing the angle of the surgical implement head relative to the longitudinal axis of the elongate body includes
 (i) a first push-pull rod; and
 (ii) a first linkage arm that is pivotably connected both to the surgical implement head and to the first push-pull rod,
 wherein pushing or pulling the first push-pull rod, pushes or pulls the first linkage arm, and the first linkage arm in turn changes the angle of the surgical implement head relative to the longitudinal axis of the elongate body, by causing it to pivot about an axis of rotation of the second joint; and
 (iii) a second push-pull rod; and
 (iv) a second linkage arm that is pivotably connected both to the surgical implement head and to the second push-pull rod,
 wherein pushing or pulling the second push-pull rod, pushes or pulls the second linkage arm, and the second linkage arm in turn changes the angle of the surgical implement head relative to the longitudinal axis of the elongate body, by causing it to pivot about an axis of rotation of the second joint in a direct opposite to that of the first pull rod and first linkage arm.

Desirably at least one and desirably each linkage arm is flush with the elongate body when the surgical implement head is not articulated (is straight) relative to the elongate body.

However it will be appreciated that a single push-pull rod may be used to effect movement of the first and second linkage arms.

Suitably, when opening and closing for gripping or cutting, one surgical implement jaw remains in a fixed position and the other moves. In such an arrangement it is desirable that the fixed jaw is the lower jaw. The lower jaw is the jaw that is lower in position, for example, in the orientation in which the device is held, for example lower in the direction that the angle relative to the longitudinal axis of the elongate body moves towards 90 degrees.

An articulating surgical implement of the invention may include a mechanism for opening and closing the surgical implement jaws that includes a pulley. Desirably the axis of rotation of the pulley is substantially coincident with the axis of rotation of the second joint. Such an arrangement allows for the transmission of an opening/closing force to the jaws of the surgical instrument even when the surgical implement head has been articulated away from a straight position.

The mechanism for opening and closing the surgical implement jaws desirably includes independently operable first and second pulleys, optionally wherein the respective axes of rotation of the first and second pulleys are substantially coincident with the axis of rotation of the second joint.

A first cable may run across the first pulley to effect movement and a second cable may run across the second pulley to effect movement.

Desirably the first pulley forms part of a mechanism that is operable to move the surgical implement head toward a first position where its longitudinal axis is at 90 degrees to the longitudinal axis of the elongate body and the second pulley forms part of a mechanism that is operable to move the surgical implement head toward a second position which is 180 degrees apart from the first position, where its longitudinal axis is at 90 degrees to the longitudinal axis of the elongate body.

The present invention thus provides a highly versatile device.

BRIEF DESCRIPTION OF THE DRAWINGS

Embodiments of the invention will be described, by way of example only, with reference to the accompanying drawings in which:

FIG. 1 is a side view of a device of the invention in the form of a rongeur which has a surgical implement head in a straight or aligned position and with the jaws in an open position and with Detail A showing an enlarged view of the surgical implement head;

FIG. 2 is a side view of a device of FIG. 1 where the surgical implement head has been moved to a 90 degree offset (upbite) position and with the jaws in an open position and with Detail B showing an enlarged view of the surgical implement head;

FIGS. 6 to 9 are perspective views of a device of the invention as in previous Figures and showing the progressive movement of the surgical implement head from a straight position (as in FIG. 6) where its longitudinal axis is substantially parallel to the longitudinal axis of the elongate body of the surgical implement and an angled position where its longitudinal axis is at 90 degrees to the longitudinal axis of the elongate body (as in FIG. 9);

FIG. 10 is a side view of a device of the invention similar to earlier figures but with two moving jaws;

DETAILED DESCRIPTION OF THE DRAWINGS

Figure 3:
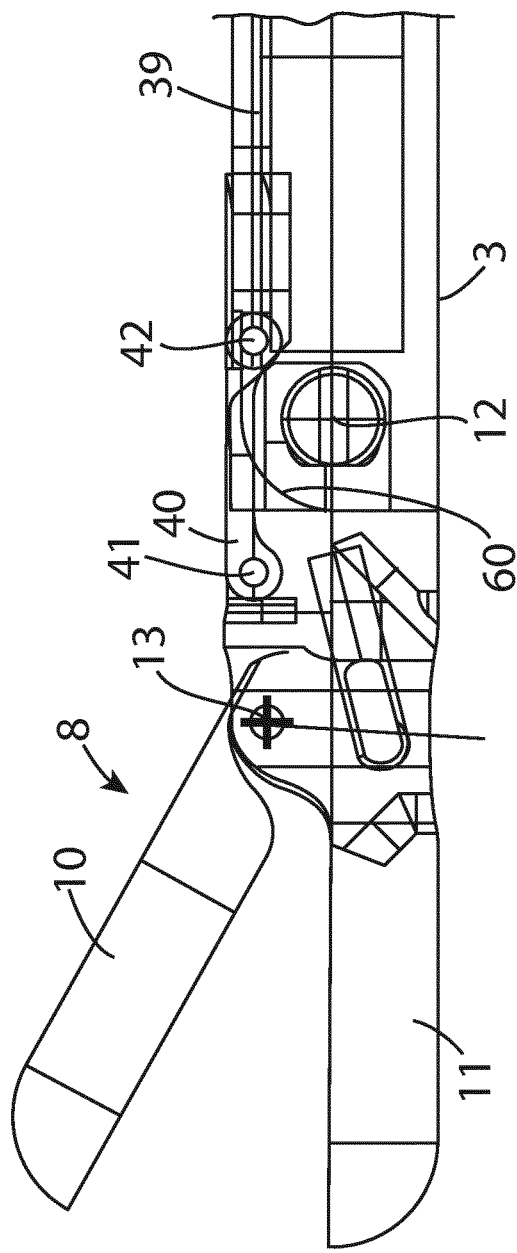
FIG. 3 is a partial and enlarged side view, showing a part-sectional view, of a device of FIG. 1 which has a surgical implement head in a straight or aligned position and with the jaws in an open position.

The present invention will now be describe in relation to the figures. It will be appreciated that different figures have been drawn to different scale.

FIG. 1 is a side view of a device of the invention which is an articulating surgical implement 1. The surgical implement 1 has an elongate body 2. As is desirable in all embodiments, the elongate body 2 is formed by a straight rigid hollow arm 3. The elongate body 2 has a proximal end 4 and a distal end 5. The elongate body to as a longitudinal axis 6.

A grip 7 is provided on the proximal end 4. The grip 7 is for holding the surgical implement. A user will hold the grip 7 in a hand.

A surgical implement head 8 is formed on the distal end 5 of the elongate body 2. The surgical implement head 8 has a base part 9 and two surgical implement jaws 10,11.

While it will be appreciated that other clamping or cutting jaws may be utilised, in the embodiment, the surgical instrument 1 takes the form of a rongeur, so the cutting jaws 10,11 are each cup-shaped and are suitable for gouging out tissue including bone tissue. The respective cup shapes 14, 15 of respective jaws 10,11 are shown in dashed outline in FIG. 5.

In the embodiment the lower jaw 11 is fixed, while the upper jaw 10 is pivotable. It will be understood that this arrangement could be reversed so that the lower jaw is pivotable while the upper jaw is fixed. It will also be understood that both jaws could be pivotable.

FIG. 10 is a side view of a surgical instrument 1 of the invention similar to earlier figures but with two moving jaws 10,11. As is possible for all embodiments the jaws 10, 11 are each pivotable about a single pivot 13 as indicated by arrow D for opening and closing. The mechanism for opening and closing the jaws 10,11 works in a manner analogous to that described above with a cable 51 running across a pulley 50 and with movement effected by the handles 26,27. In this case pulling the link coupling 53 (by squeezing the handles 26,27) closes the jaws 10,11 while opening the handles pushes the link coupling and opens the jaws 10,11.

Desirably a balancing mechanism operates to ensure the two jaws open and close by the same amount. For example each jaw may have a lever arm and the lever arms may be connected together for example with a single slotted bar that may then the fixing point for the cable. The connection between lever arms and the slotted bar allows for the balancing movement As is possible for all embodiments the jaws 10,11 are connected by a biasing member 65 in the form of two interconnected leaf spring portions 66,67. The biasing member 65 resiliently biases or spring loads the jaws 10,11 towards the open position shown in FIG. 10. Closing of the jaws 10,11 takes place against that biasing action. It will be appreciated that in such an arrangement the biasing member is arranged to apply an opening force to a jaw or jaws that open. In this way the mechanism for opening and closing the jaws is biased toward the open position. This is advantageous as with the biasing member present a squeezing action of the handles will compress the biasing member and releasing the squeezing action on the handles 26,27 will automatically allow the jaws to return to an open position under the biasing action of the biasing member.

The surgical implement head 9 having a first joint in the form of a pivot or hinge 13 that allows relative movement of the surgical jaws and in particular movement of the surgical implement jaw 10 to move relative to the fixed jaw 11 thus allowing the jaws 10 and 11 to open and close for gripping and cutting.

A second joint in the form of a pivot or hinge 12 is provided on the distal end 5 of the elongate body 2. This hinge 12 allows for articulation of the device. In particular it allows for change of the angle of the surgical implement head 2 relative to the longitudinal axis 6 of the elongate body 2. In particular the hinge 12 allows articulation or pivoting of the surgical head 8 so that it can be moved from the position shown in FIG. 1 where it is a straight/aligned position relative to the elongate body 2 to a position at which it is at 90 degrees to the elongate body 2 (the position shown in FIG. 2). More particularly it allows the surgical head 8 to move so that a longitudinal axis 16 of the surgical head 8 moves from a position in which it is substantially aligned or coincident with the longitudinal axis 6 of the elongate body 2 as shown in FIG. 1 to a position in which the longitudinal axis 16 of the surgical head 8 is at 90 degrees to the longitudinal axis 6 of the elongate body 2 (the position shown in FIG. 2). In later figures the hinge 12 allows for movement to a downbite position as will be described in more detail below.

It will be appreciated that the device of the invention that is illustrated allows for articulation to an upbite position. It will be appreciated that a device of the invention could easily be configured for articulation to a downbite position. (For a downbite any configuration of the jaws as describe above may be used but it may be desirable that the upper jaw is fixed and the lower jaw is pivotable.) Handles may be moved down too.

The grip 7 comprises an end piece 20. The elongate body 2 projects away from a nose portion 21 of the end piece 20. The grip 7 comprises a pair of handles 26, 27 which are designed to be gripped by a user. The handle 27 fits into the palm of the hand of a user. A user's fingers extend about the handle 26. A stub 25 projecting rearwardly from the grip 7 forms a rest that rests against the bridge of the hand between the thumb and first finger of a user helping with a better grip by the user.

The handle 26 is movable (as indicated by arrow A) and is for opening and closing the jaws 10, 11 as will be described in more detail below. It pivots about pivot point 28.

Three fasteners such as rivets or pins 29a; 29b;29c secure the grip together and hold it to the elongate body 2.

A control lever 35 is held by a fastener 36 (such as a grub screw) to the grip 7 and is pivotable relative to the grip 7 as indicate by Arrow B in FIG. 2 and Arrow C in FIG. 1. It has a knob or dial 38 that allows it to be pivoted by manual rotation. It forms part of a mechanism for changing the angle of the surgical implement head relative to the longitudinal axis of the elongate body as will be described in more detail below. The control lever can be (reversibly) moved between the position shown in FIG. 1 and that of FIG. 2. It can be moved to any intermediate position. It will remain at the selected position for example by frictional engagement relative to the grip 7.

A mechanism for changing the angle of the surgical implement head 8 relative to the longitudinal axis 6 of the elongate body 2 is provided.

Figure 4:
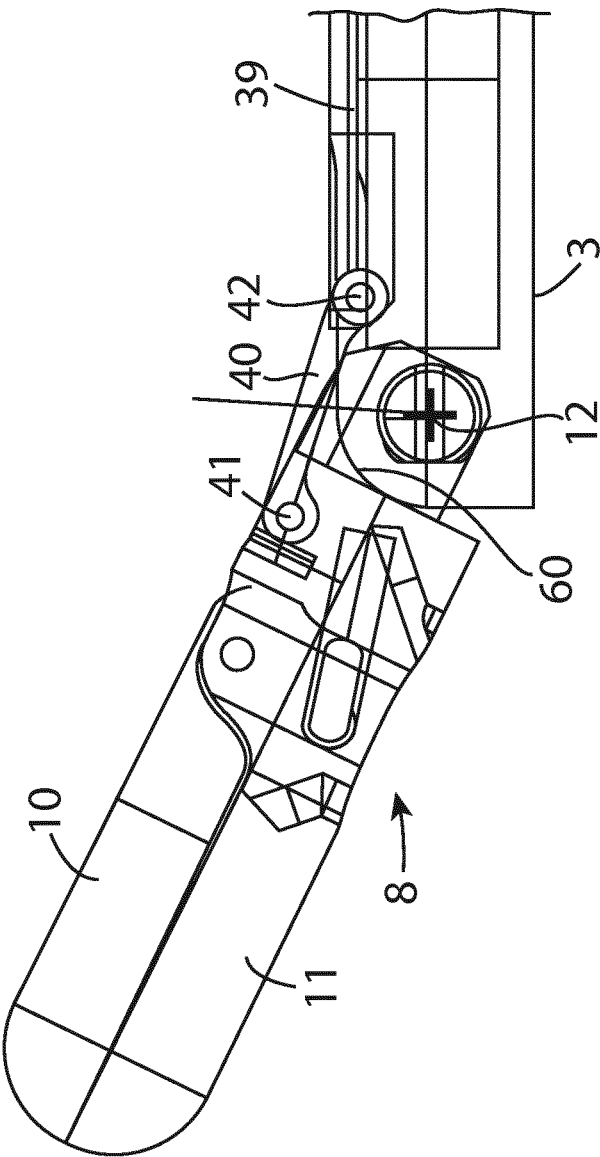
FIG. 4 is a partial and enlarged side view, showing a part-sectional view, of a device of FIG. 1 which has a surgical implement head in an offset position and with the jaws in a closed position.
Figure 5:
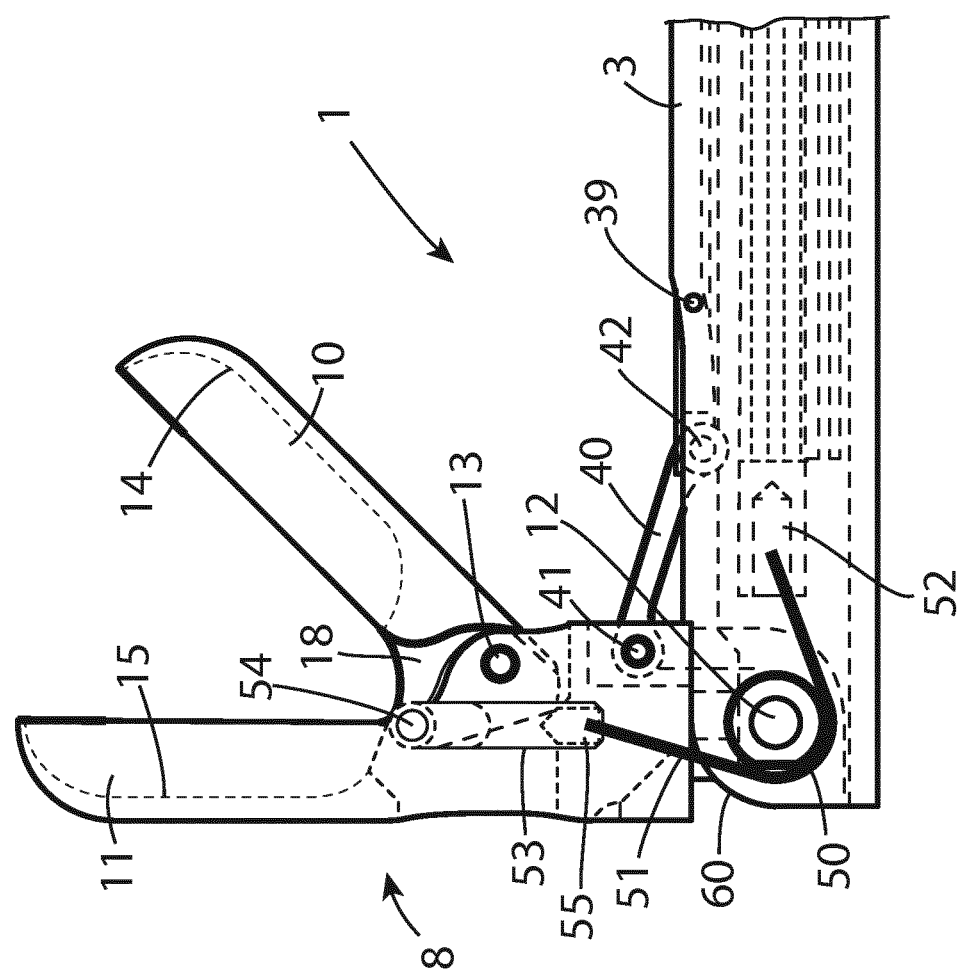
FIG. 5 is a partial and enlarged side view, showing a part-sectional view, of a device of FIG. 1 which has a surgical implement head in a 90 degree offset position and with the jaws in an open position and showing in detail a mechanism for a mechanism for opening and closing the jaws.
Figure 6:
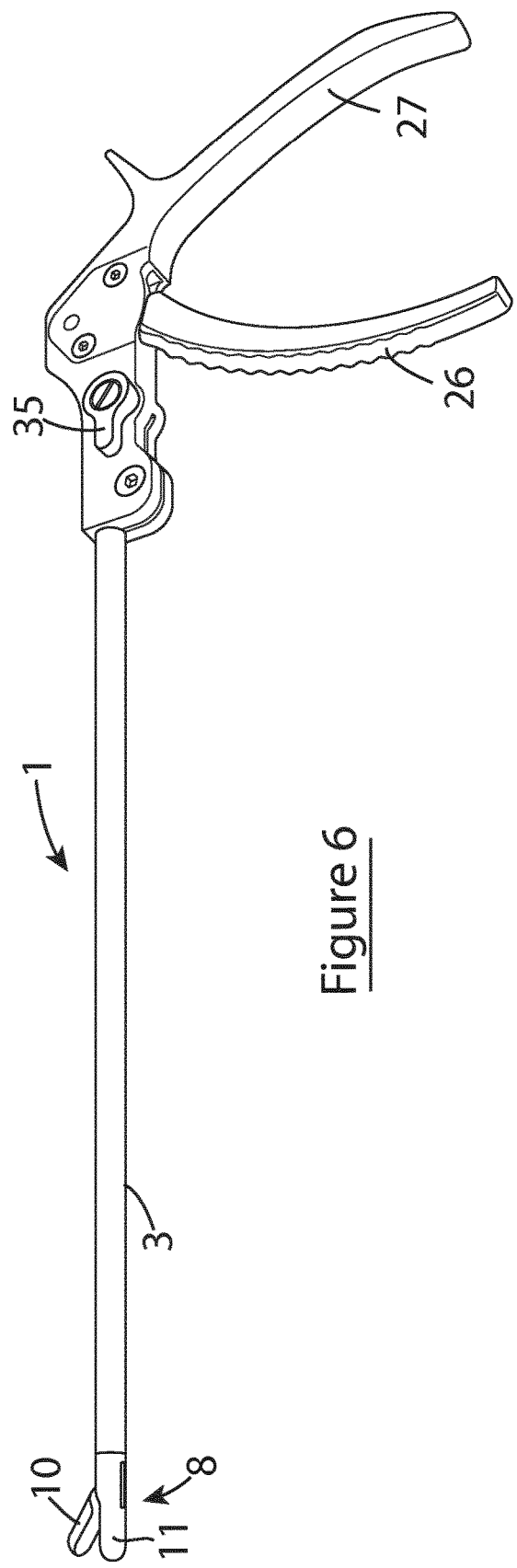

The mechanism comprises the control lever 35, a control rod 39 and a linkage arm 40 (best seen in FIGS. 3, 4 and 5). The control rod 39 runs (hidden) within the elongate hollow arm 3. The control lever 35 is connected to the control rod 39 on the grip 7 side of the proximal end 4 of the elongate hollow arm 3. The linkage arm 40 is connected to both the surgical implement head 8 and the control rod 39 so that an angular range of movement of the control lever 35 about the fastener 36 effects an angular range of movement of the surgical implement head 8 by pivoting about an axis of rotation of the second joint in the form of the pivot or hinge 12.

Pushing or pulling the control rod 39, changes the angle of the surgical implement head 8 relative to the longitudinal axis 6 of the elongate body 2, by causing it to pivot about an axis of rotation of the second joint in the form of the pivot or hinge 12.

The linkage arm 40 is pivotably connected by a pivot joint 41 to the surgical implement head 8 and is pivotably connected by a pivot joint 42.

In the position of the control lever 35 shown in FIG. 1 a longitudinal axis 37 of the control lever 25 is substantially parallel to the longitudinal axis 6 of the elongate body 2. The longitudinal axis 16 of the surgical implement head 8 is parallel to and substantially aligned with the longitudinal axis 6 of the elongate body 2.

Rotating the control lever 35 (in the direction of Arrow A which is clockwise from the perspective of the drawings) to the position shown in FIG. 2 pulls the control rod 39 rearwardly in a direction towards the grip 7. This in turn causes the linkage arm 40 to be pulled in the same direction. This causes the surgical implement head 8 to be pulled in the same direction also. This changes the angle of the surgical implement head 8 relative to the longitudinal axis 6 of the elongate body 2, by causing it to pivot about an axis of rotation of the second joint in the form of the pivot or hinge 12.

It will be noted that the linkage arm 40 is substantially flush with the elongate body 2 in the position shown in FIG. 1. As the linkage arm 40 is pulled by the control rod 39, it becomes raised, at an angle. It triangulates between the (longitudinal axis of the) control rod 39, the pivot point 12 and the longitudinal axis 16 of the surgical implement head 8.

Starting with the position shown in FIG. 2 and rotating the control lever 35 (in the direction of Arrow B which is anticlockwise from the perspective of the drawings) to the position shown in FIG. 1 pushes the control rod 39 forward in a direction away from the grip 7. This in turn causes the linkage arm 40 to be pushed in the same direction. This causes the surgical implement head 8 to be pushed in the same direction also. This changes the angle of the surgical implement head 8 relative to the longitudinal axis 6 of the elongate body 2, by causing it to pivot about an axis of rotation of the second joint in the form of the pivot or hinge 12. The surgical instrument head 8 is then straight relative to the elongate body 2. It will be noted that the linkage arm 40 returns to the position where it is substantially flush with the elongate body 2 (in the position shown in FIG. 1).

It will be appreciated that as the control lever 35 is rotated, there is a corresponding rotation/articulation of the surgical head 8. Accordingly, the surgical head 8 can be articulated to a position intermediate the position shown in FIGS. 1 and 2. It is desirable that the angle of the longitudinal axis 37 of the control lever 35 relative to the longitudinal axis 6 of the elongate body 2 is the same as the angle of the longitudinal axis 16 of the surgical head 8 relative to the longitudinal axis 6 of the elongate body 2 as this makes use more intuitive for a user. The position of the control lever relative to the elongate body reflects the position of the head relative to the elongate body.

Having the linkage arm 40 flush with the elongate body 2 is desirable from the point of view of inserting and retracting the surgical implement 1 to and from a target site.

A mechanism is also provided for opening and closing the surgical implement jaws. Desirably the mechanism is operable through the angular range of movement of the surgical instrument head.

As is desirable in all embodiments, the mechanism for opening and closing the surgical implement jaws includes a pulley. As best seen in FIG. 5 the mechanism for opening and closing the surgical implement jaws 10,11 includes a pulley wheel 50. The axis of rotation of the pulley wheel 50 is substantially coincident with the axis of rotation of the second joint 12. A flexible push/pull wire or cable 51 runs across pulley wheel 50. The push/pull wire 51 runs through the rigid hollow arm 3 of the implement 1. The push/pull wire is connected to the moveable handle 26 on the grip. Movement of the handle causes the push/pull wire 51 to move. The pulley wheel 50 turns to allow the movement and in particular to allow the push/pull wire 51 to operate even when the surgical implement head 8 is at an angle to the elongate body 2.

The push/pull wire 51 is connected to a link coupling 53 at a lower end 55 thereof. The link coupling 53 is pivotally connected at its upper end 54 to a crotch area 18 of the surgical implement head 8. As the handle 26 is operated as indicated by Arrow A (see FIG. 1) it moves the jaws from the open to the closed (biting) position. So squeezing the two handles 26,27 causes the cable 51 to be pulled in a direction away from the jaws 10,11, this pulls link coupling 53 which in turn cause jaw 10 to close by pivoting about joint 13. Moving the handles 26,27 apart causes the cable 51 to be pushed in a direction towards the jaws 10,11, this pushes link coupling 53 which in turn causes jaw 10 to open by pivoting about joint 13 thus opening jaw 10 relative to jaw 11. This opening and closing of jaw 10 can be effected at any relative position of the surgical implement head 8 to the elongate body 2.

It will be appreciated that the push/pull wire 51 is sufficiently rigid to allow opening and closing of the jaws, but on the other hand is sufficiently flexible to operate about the pulley wheel at a range of different angles.

The control rod 39 and/or push/pull wire 51 can be any suitable form such as a woven cable with minimal length alteration in pull or push motion. It might be of solid or composite material with flexible characteristics, but minimal alteration in pull or push motion (metals, including, shape memory metals such as Nitinol, ultraflexible steel, sintered bronze, and composite materials, plastics, and ceramics).

The control rod and/or the push/pull wire 51 might be guided in a Bowden wire fashion. It may be a cable configuration with minimal friction, whereas the cable might be coated, sheathed or surface treated.

The pulley wheel maybe made of various materials, including metals such as steel or sintered bronze, composite materials, plastics, or ceramics.

In the embodiment (see FIG. 5) the push/pull wire 51 is guided in a Bowden wire fashion being housed within and slidable relative to an outer cable 52.

It will be noted from the drawings, and FIGS. 3 to 5 in particular, that the distal end 5 of the elongate body 2/rigid hollow arm 3 has a cammed profile, in the form of a curved surface which is curved in the direction of movement of the surgical implement head 8, to allow the surgical implement head 8 to articulate relative to the elongate body 2/rigid hollow arm 3.

Figure 7:
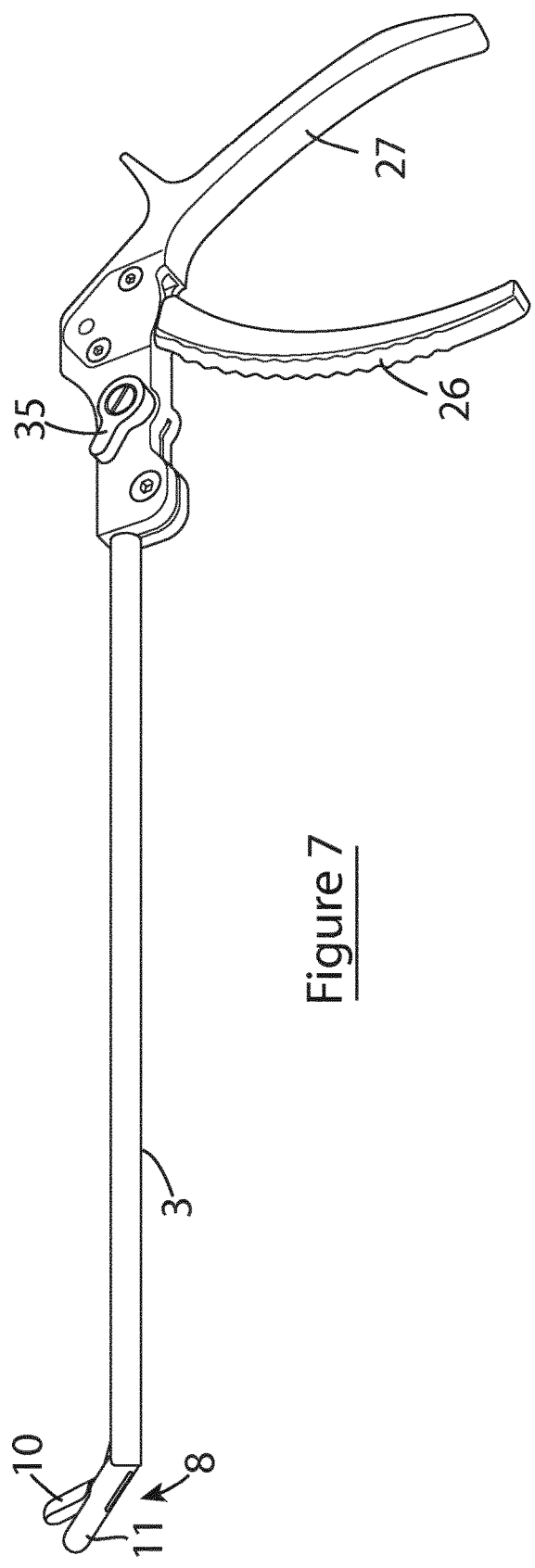

FIGS. 6 to 9 show the progressive movement of the surgical implement head 8 from a straight position (as in FIG. 6) where its longitudinal axis 16 is substantially parallel to the longitudinal axis 6 of the elongate body 2 of the surgical implement 1 and an angled position where its longitudinal axis 16 is at 90 degrees to the longitudinal axis 6 of the elongate body (as in FIG. 9).Figures 7 and 8 show intermediate positions. It will be noted from the progression shown that the jaws 10,11 are operable across the range of movement of the surgical implement head 8.

It will be also noted that in FIGS. 6 to 9 the position of the control lever 35 relative to the elongate body 2 corresponds to the position of the surgical implement head 8 relative to the elongate body 2.

FIGS. 11 to 15 show a surgical implement 1 of the invention wherein the angular range of movement of the (longitudinal axis 16 of the) surgical implement head 8 is 180 degrees relative to the longitudinal axis 6 of the elongate body 2. The surgical head 8 can move from an upbite position (as in FIGS. 11, 13 and as shown in dashed outline in FIG. 15) where it is at 90 degrees above the elongate body through a straight position (shown in dashed outline in FIG. 15) where it is aligned with the elongate body to a downbite position (as in FIGS. 12, 14 and shown in full outline in FIG. 15) where it is at 90 degrees below the elongate body. Arrow E shows the direction of movement from an upbite position towards downbite position. Arrow F shows the direction of movement from a downbite position towards an upbite position.

As used herein upbite is use to refer to the ability to articulate the surgical implement head above the elongate body relative to the handles 26,27. The surgical implement head articulates up and away from the handles. As used herein downbite is use to refer to the ability to articulate the surgical implement head below the elongate body relative to the handles 26,27. The surgical implement head articulates down and towards the handles 26,27. It can be considered that the longitudinal axis of the surgical implement head moves from a +90 degree angle to −90° degree angle relative to the longitudinal axis of the elongate body.

Figure 11:
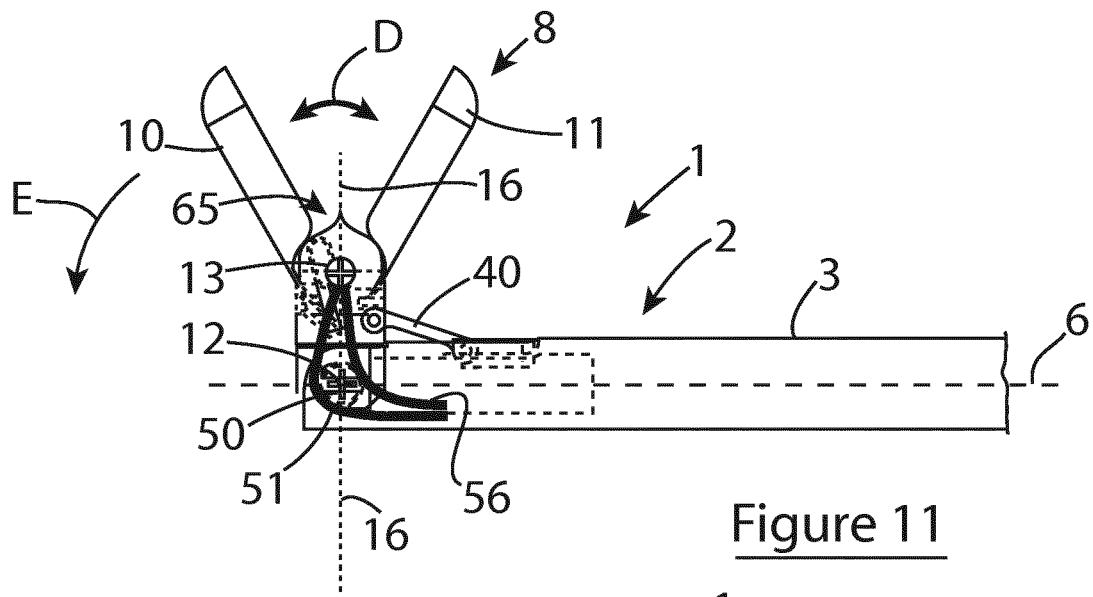
FIG. 11 is a partial and enlarged side view, showing a part-sectional view of a device of the invention wherein the angular range of movement of the surgical implement head is 180 degrees relative to the longitudinal axis of the elongate body and the device is in an upbite position with open jaws.
Figure 12:
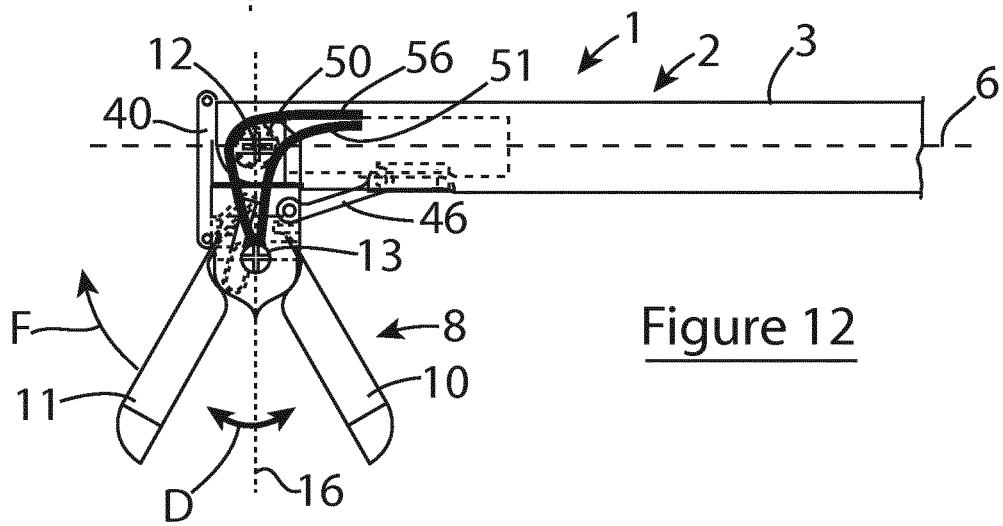
FIG. 12 is a side view similar to that of FIG. 11 where the surgical implement head has been moved from the position of FIG. 11 to a second position which is 180 degrees apart from the first position, and the device is in a downbite position with open jaws.

FIGS. 11 and 12 show the mechanism for opening and closing the surgical implement jaws 10,11. (The jaws 10 and 11 both open and close as described above with respect to FIG. 10.)

In this case there is a dual pulley wheel 50 (again the axis of rotation of the pulley wheel 50 is substantially coincident with the axis of rotation of the second joint 12) which allows the cable 51 to be operated in the manner described above for the upbite position of FIG. 11. The dual pulley wheel allows dual cables to be operated independently. For example the dual pulley wheel could take the form of two grooved wheels which are independently rotatable.

In the downbite position of FIG. 12 a second cable 56 engages with the dual pulley wheel 50 so that the cable 56 effects opening of closing of the jaws 10,11 in the downbite position.

It will be appreciated that the dual cables form part of a mechanism for opening and closing the surgical implement jaws 10, 11 in a manner analogous to that described above. Squeezing the handles 26, 27 together while the surgical implement head 8 is in the upbite position will cause the cable 51 to effect closure of the jaws. Squeezing the handles 26, 27 together while the surgical implement head 8 is in the downbite position will cause the cable 56 to effect closure of the jaws. In any position of the surgical implement head 8 the biasing means 65 will bias the jaws 10, 11 back towards the open position when the squeezing force is removed. Optionally the respective axes of rotation of the first and second pulleys are substantially coincident with the axis of rotation of the second joint.

These form independent mechanisms and may respectively be for effecting opening and closing of the jaws in an upbite and downbite position of the surgical implement head.

For example the first pulley may form part of a mechanism that is operable to move the surgical implement head toward a first position (, for example an upbite position) where its longitudinal axis is at 90 degrees to the longitudinal axis of the elongate body and the second pulley forms part of a mechanism that is operable to move the surgical implement head toward a second position (, for example a downbite position) which is 180 degrees apart from the first position, where its longitudinal axis is at 90 degrees to the longitudinal axis of the elongate body.

As is desirable for all embodiments the two mechanisms together allow opening and closing of the jaws across 180 degrees of movement of the surgical implement head. They are independently operable and articulation of the surgical implement head (from an upbite to a downbite position and vice versa) automatically engages the part of the mechanism that operates in that position (whilst disengaging the other part of the mechanism).

Figure 13:
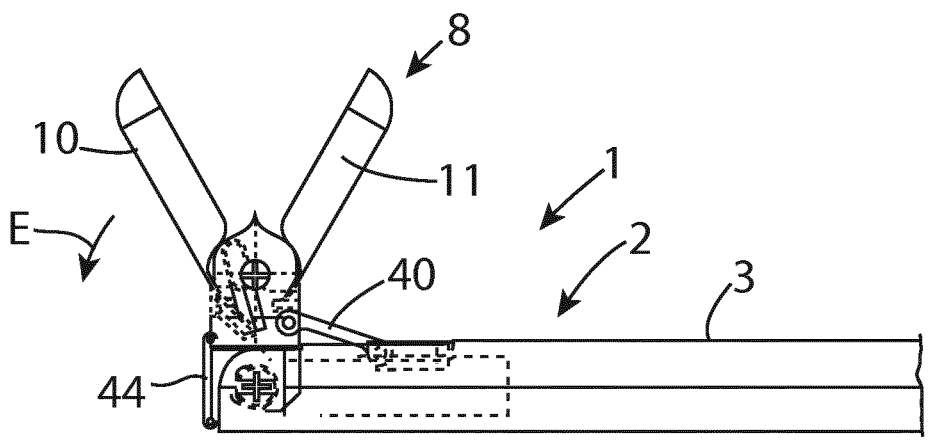
FIG. 13 is a side view similar to that of FIG. 11 showing in more detail the mechanism for changing the angle of the surgical implement head relative to the longitudinal axis of the elongate body.
Figure 14:
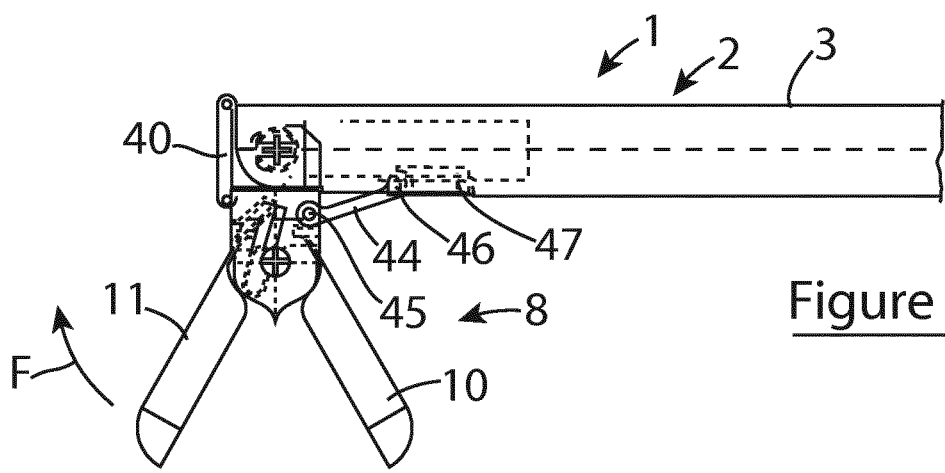
FIG. 14 is a side view similar to that of FIG. 12 showing in more detail the mechanism for changing the angle of the surgical implement head relative to the longitudinal axis of the elongate body.

FIGS. 13 and 14 show in more detail the mechanism for changing the angle of the surgical implement head 8 relative to the longitudinal axis 6 of the elongate body 2. The mechanism comprises mechanism described above and in addition a second control rod 47 and a second linkage arm 44. The control rod 44 runs (hidden) within the elongate hollow arm 3. The control lever 35 is connected to the control rod 44 on the grip 7 side of the proximal end 4 of the elongate hollow arm 3. The linkage arm 44 is connected (on the opposite (lower) side of the surgical implement 1) to both the surgical implement head 8 and the control rod 44 so that an angular range of movement of the control lever 35 about the fastener 36 effects an angular range of movement of the surgical implement head 8 by pivoting about an axis of rotation of the second joint in the form of the pivot or hinge 12.

It will be appreciated that a single control rod can be used to effect movement of both linkage arms.

Pushing or pulling the control rod 44, changes the angle of the surgical implement head 8 relative to the longitudinal axis 6 of the elongate body 2, by causing it to pivot about an axis of rotation of the second joint in the form of the pivot or hinge 12.

The control rod 44 and the linkage arm 44 move the surgical implement head 8 to and from the downbite position. The control rod 39 and the linkage arm 40 move the surgical implement head 8 to and from the upbite position The linkage arm 44 is pivotably connected by a pivot joint 45 to the surgical implement head 8 and is pivotably connected by a pivot joint 46 to control rod 47.

Rotating the control lever 35 in the direction of Arrow B (which is anticlockwise from the perspective of the drawings) from the position shown in FIG. 1 pulls the control rod 47 rearwardly in a direction towards the grip 7. This in turn causes the linkage arm 44 to be pulled in the same direction. This causes the surgical implement head 8 to be pulled in the same direction also. This changes the angle of the surgical implement head 8 relative to the longitudinal axis 6 of the elongate body 2, by causing it to pivot about an axis of rotation of the second joint in the form of the pivot or hinge 12 to a downbite position. Rotating the control lever 35 in the direction of Arrow A (which is clockwise from the perspective of the drawings) from the downbite position will move the surgical implement head 8 back towards the straight position.

Figure 15:
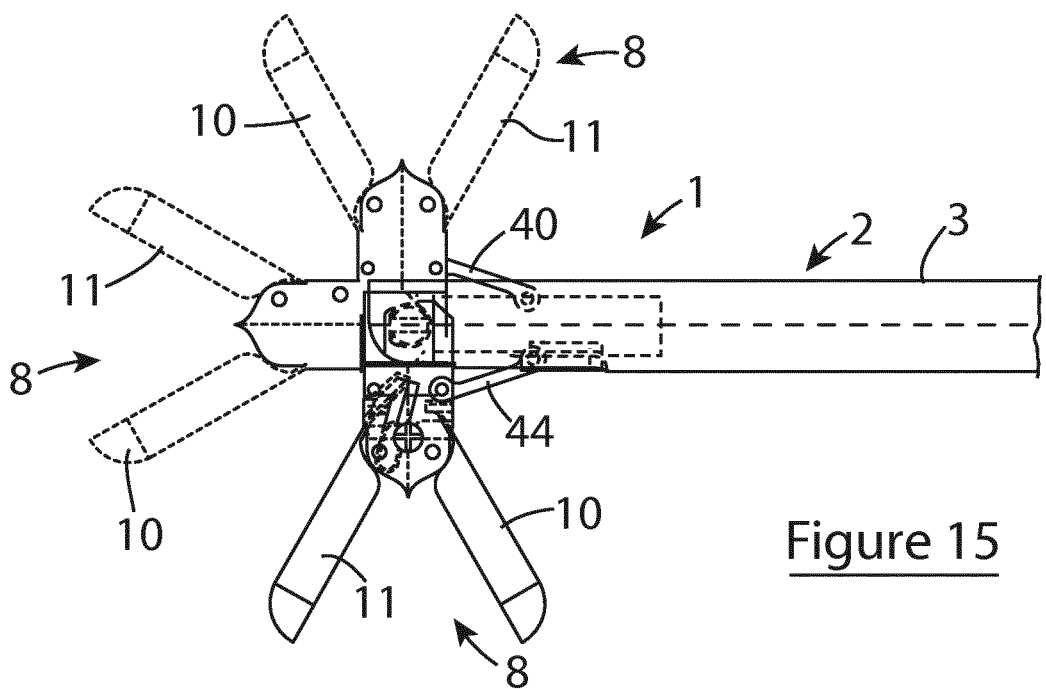
FIG. 15 is a side view similar to that of FIGS. 11 to 14 showing the articulation of the surgical implement head.

It will be noted that the linkage arm 44 is substantially flush with the elongate body 2 in the straight position shown in dashed outline in FIG. 15. As the linkage arm 44 is pulled by the control rod 47, it becomes raised, at an angle. It triangulates between the (longitudinal axis of the) control rod 47, the pivot point 12 and the longitudinal axis 16 of the surgical implement head 8.

It will be appreciated (, and as best seen in FIG. 14) that the respective control rod/linkage arms 39,40 and 47,44 operate on opposite sides of the device to effect upbite and down bite respectively. Neither should interfere with the other, and as can be seen from FIG. 14 linkage arm 40 is pulled around the distal end 5 of the elongate body 2 when the downbite position is effected. The reverse occurs when the upbite position is selected with the linkage arm 44 pulled around the distal end 5 of the elongate body 2 as shown in FIG. 13.

In use, the surgical implement 1 is introduced to a target site. Typically it will be in the straight (FIG. 1) configuration and with the jaws closed. The user can then set the angle at which it is desired to operate and adjust accordingly. The implement can be used to clamp, cut or bite by operating the handles 26, 27. Alternatively, the angle at which it is desired to operate can be preselected and thus pre-set before the surgical instrument is introduced to a target site. It will also be appreciated that the relative position of the surgical implement head can be adjusted to two or more different relative positions so as to work over the entire target area. Both upbite and downbite angles can be selected. In effect the device can work around a corner, i.e. work at a position offset from the longitudinal axis of the device, so from a given point of access the surgical implement head can be turned relative to the remainder of the device to grip or cut at a target site.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

We claim:

1. An articulating surgical implement comprising:
   (i) an elongate body having a proximal end and a distal end and a longitudinal axis;
   (ii) a grip on the proximal end for holding the surgical implement;
   (iii) a surgical implement head formed on the distal end of the elongate body, and having surgical implement jaws, the surgical implement head having a first joint with an axis of rotation that allows the surgical implement jaws to move relative to each other to open and close for gripping or cutting;
   (iv) a second joint on the distal end of the elongate body for changing the angle of the surgical implement head relative to the longitudinal axis of the elongate body;
   (v) a mechanism for changing the angle of the surgical implement head relative to the longitudinal axis of the elongate body through an angular range of movement by pivoting about an axis of rotation of the second joint; and
   (vi) a mechanism for opening and closing the surgical implement jaws wherein the mechanism for opening and closing the surgical implement jaws includes a pulley; and
   wherein the axis of rotation of the pulley is substantially coincident with the axis of rotation of the second joint and further wherein the axis of rotation of the first joint is parallel to the axis of rotation of the pulley.

2. An articulating surgical implement according to claim 1 wherein the mechanism for opening and closing the surgical implement jaws is operable through the angular range of movement.

3. An articulating surgical implement according to claim 1 wherein the angular range of movement is 90 degrees relative to the longitudinal axis of the elongate body so that the surgical implement head can be moved to a position where its longitudinal axis is at 90 degrees to the longitudinal axis of the elongate body.

4. An articulating surgical implement according to claim 1 wherein the surgical implement head is moveable between a straight position where its longitudinal axis is substantially parallel to the longitudinal axis of the elongate body and an angled position where its longitudinal axis is at 90 degrees to the longitudinal axis of the elongate body.

5. An articulating surgical implement according to claim 1 wherein the angular range of movement is 180 degrees relative to the longitudinal axis of the elongate body so that the surgical implement head can be moved from a first position where its longitudinal axis is at 90 degrees to the longitudinal axis of the elongate body to a second position which is 180 degrees apart from the first position, where its longitudinal axis is at 90 degrees to the longitudinal axis of the elongate body.

6. An articulating surgical implement according to claim 1 wherein the mechanism for changing the angle of the surgical implement head relative to the longitudinal axis of the elongate body includes a first rod, and pushing or pulling the first rod, changes the angle of the surgical implement head relative to the longitudinal axis of the elongate body, by causing it to pivot about an axis of rotation of the second joint; and optionally wherein:
   the mechanism for changing the angle of the surgical implement head relative to the longitudinal axis of the elongate body includes a second rod, and pushing or pulling the second rod, changes the angle of the surgical implement head relative to the longitudinal axis of the elongate body, by causing it to pivot about an axis of rotation of the second joint in a direction opposite to the first rod.

7. An articulating surgical implement according to claim 1 wherein the mechanism for changing the angle of the surgical implement head relative to the longitudinal axis of the elongate body includes a first linkage arm that is pivotably connected to the surgical implement head; and
   optionally wherein:
   the mechanism for changing the angle of the surgical implement head relative to the longitudinal axis of the elongate body includes a second linkage arm that is pivotably connected to the surgical implement head causing it to pivot about an axis of rotation of the second joint in a direction opposite to the first linkage arm.

8. An articulating surgical implement according to claim 7 wherein at least one and desirably each linkage arm is flush with the elongate body when the surgical implement head is not articulated relative to the elongate body.

9. An articulating surgical implement according to claim 1 wherein the mechanism for changing the angle of the surgical implement head relative to the longitudinal axis of the elongate body includes:
(i) a push-pull rod; and
(ii) a linkage arm that is pivotably connected both to the surgical implement head and to the push-pull rod, wherein pushing or pulling the push-pull rod, pushes or pulls the linkage arm, and the linkage arm in turn changes the angle of the surgical implement head relative to the longitudinal axis of the elongate body, by causing it to pivot about an axis of rotation of the second joint and optionally wherein:
the mechanism for changing the angle of the surgical implement head relative to the longitudinal axis of the elongate body includes
(i) a first push-pull rod; and
(ii) a first linkage arm that is pivotably connected both to the surgical implement head and to the first push-pull rod, wherein pushing or pulling the first push-pull rod, pushes or pulls the first linkage arm, and the first linkage arm in turn changes the angle of the surgical implement head relative to the longitudinal axis of the elongate body, by causing it to pivot about an axis of rotation of the second joint; and
(i) a second push-pull rod; and
(ii) a second linkage arm that is pivotably connected both to the surgical implement head and to the second push-pull rod, wherein pushing or pulling the second push-pull rod pushes or pulls the second linkage arm, and the second linkage arm in turn changes the angle of the surgical implement head relative to the longitudinal axis of the elongate body, by causing it to pivot about an axis of rotation of the second joint in a direct opposite to that of the first pull rod and first linkage arm.

10. An articulating surgical implement according to claim 1, wherein, when opening and closing for gripping or cutting, one surgical implement jaw remains in a fixed position and the other moves; and optionally wherein:
the fixed jaw is the lower jaw.

11. An articulating surgical implement according to claim 1 wherein a cable runs across the pulley to effect movement.

12. An articulating surgical implement according to claim 1 wherein the mechanism for opening and closing the surgical implement jaws includes independently operable first and second pulleys, optionally wherein the respective axes of rotation of the first and second pulleys are substantially coincident with the axis of rotation of the second joint.

13. An articulating surgical implement according to claim 12 wherein a first cable runs across the first pulley to effect movement and the second cable runs across the second pulley to effect movement.

14. An articulating surgical implement according to claim 12 - wherein the first pulley forms part of a mechanism that is operable to move the surgical implement head toward a first position where its longitudinal axis is at 90 degrees to the longitudinal axis of the elongate body and the second pulley forms part of a mechanism that is operable to move the surgical implement head toward a second position which is 180 degrees apart from the first position, where its longitudinal axis is at 90 degrees to the longitudinal axis of the elongate body.

* * * * *